United States Patent
Mishelevich

(10) Patent No.: US 7,248,171 B2
(45) Date of Patent: Jul. 24, 2007

(54) RFID SYSTEMS FOR AUTOMATICALLY TRIGGERING AND DELIVERING STIMULI

(76) Inventor: David J. Mishelevich, 7301 Vista del Mar., #B111, Playa del Rey, CA (US) 90293

( * ) Notice: Subject to any disclaimer, the term of this patent is extended or adjusted under 35 U.S.C. 154(b) by 0 days.

(21) Appl. No.: 10/848,251

(22) Filed: May 17, 2004

(65) Prior Publication Data

US 2005/0280544 A1    Dec. 22, 2005

(51) Int. Cl.
*G08B 23/00*    (2006.01)

(52) U.S. Cl. .............. 340/573.1; 340/686.6; 340/572.1; 235/375

(58) Field of Classification Search ............. 340/573.1, 340/686.1, 572.1, 5.2, 5.61, 686.6; 235/375, 235/150
See application file for complete search history.

(56) References Cited

U.S. PATENT DOCUMENTS

| | | | |
|---|---|---|---|
| 3,963,033 A | | 6/1976 | Pope |
| 4,163,449 A | | 8/1979 | Regal |
| 4,995,404 A | | 2/1991 | Nemir |
| 5,243,998 A | | 9/1993 | Silverman |
| 5,304,211 A | | 4/1994 | Israel et al. |
| 5,351,653 A | | 10/1994 | Marischen et al. |
| 5,353,744 A | | 10/1994 | Custer |
| 5,949,335 A | * | 9/1999 | Maynard ............. 340/572.1 |
| 6,034,622 A | | 3/2000 | Levine |
| 6,154,676 A | | 11/2000 | Levine |
| 6,166,643 A | | 12/2000 | Janning et al. |
| 6,294,999 B1 | | 9/2001 | Yarin et al. |
| 6,334,073 B1 | | 12/2001 | Levine |
| 6,380,858 B1 | | 4/2002 | Yarin et al. |
| 6,570,487 B1 | * | 5/2003 | Steeves ............. 340/5.2 |
| 2001/0028308 A1 | | 10/2001 | De La Huerga |
| 2002/0026330 A1 | | 2/2002 | Klein |
| 2002/0169583 A1 | | 11/2002 | Gutta et al. |
| 2002/0189612 A1 | | 12/2002 | Rand |
| 2003/0079744 A1 | | 5/2003 | Bonney et al. |
| 2003/0099158 A1 | | 5/2003 | De La Huerga |
| 2004/0078219 A1 | | 4/2004 | Kaylor |

OTHER PUBLICATIONS

Smith, J.W., & Frawley, P.J., "Long-Term Abstinence from Alcohol in Patients Receiving Aversion Ther. as Part of a Multimodal Inpat. Prog.," Subst. Abuse Rx, 7:77-82, 1990.
Smith, J.W., "Long-Term Outcome of Clients Treated in a Commerical Stop Smoking Program," J. Substance Abuse Treatment 5:33-36, 1998.
Frawley, P.J., & Smith, J.W., "One-Year Follow-Up after Multimodal Inpat. Treatment for Cocaine and Methamphetamine Dependencies," J Substance Abuse Treatment, 9:271-286, 1992.
"RFID Chips Watch Grandma Brush Teeth," NewScientist.com News Service, 11:50, Mar. 17, 2004.

* cited by examiner

*Primary Examiner*—Anh V. La

(57) ABSTRACT

Systems using RFID tags to identify subjects or objects using RFID readers located on a subject or in a suitable enclosure with associated host computers, stimulus generators and associated output devices are provided. The interactions can generate immediate or delayed stimuli involving one or more output types as well as recording of events.

27 Claims, 4 Drawing Sheets

US 7,248,171 B2

RFID SYSTEMS FOR AUTOMATICALLY TRIGGERING AND DELIVERING STIMULI

CROSS REFERENCE TO RELATED APPLICATIONS

Not Applicable

FEDERALLY SPONSORED RESEARCH

Not Applicable

SEQUENCE LISTING OF PROGRAM

Not Applicable

BACKGROUND OF THE INVENTION

1. Field of the Invention

This invention relates to systems providing automatic triggering and delivery of stimuli, specifically to those that incorporate RFID (Radio-Frequency Identification) techniques.

2. Background of the Invention

Radio-Frequency Identification (RFID) technology has benefited from the increased functionality and decreased costs of RFID tags and readers due to rapid expansion of the use of RFID systems for inventory, logistical tracking, and other supply chain and related functions. Expanded use of RFID tags in various formats for inventory and tracking means tags are relatively inexpensive (and in the future even more so due to in-process Wal-Mart and Department of Defense implementations) and thus their uses other applications economically practical. A passive RFID tag includes a chip and an antenna When exposed to and energized by radio-frequency (RF) energy from the RFID reader, the tag transmits its identification (possibly encrypted) which is captured by the RFID reader. A tag may have either read functionality or read/write functionality. In the latter case, data can be recorded (using its write mode) in the RFID tag itself that can be read by an RFID reader at a later time. An active RFID tag operates in the same manner as a passive RFID tag, except it has its own power source, say a battery. An active RFID tag and can be identified over long distances.

Tracking and event recording in the supply chain have been the major focus of RFID implementations. Intel has demonstrated technology ("RFID Chips Watch Grandma Brush Teeth," *NewScientist.com News Service*, 11:50, Mar. 17, 2004) in which an elderly person wears a glove-embedded RFID reader (or perhaps a necklace or other convenient carrier) that detects objects that the subject touches and wirelessly communicates the unique IDs of those objects to a personal computer that records and timestamps the events. In some cases, an ordered series of object-event occurrences is used to infer the performance of complex tasks such as brushing teeth. Aversive or appetitive stimuli are not included in this system.

Feedback triggered due to human or animal behavior can provide a positive or negative stimulus. Positive or negative stimuli can be used to give an immediate sign or for behavior modification. An example of its application for the latter is alcoholism. In the case of aversion therapy, if a person touching a drink triggers a negative stimulus, then the stimulus is paired to the act and behavior thus modified. While one can ask the question why a person would put themselves into a situation where they would get such feedback, a large subset of addicts wish to quit (e.g., smokers) or are in controlled situations such as drug rehabilitation programs. If the feedback stimulus is electrical, the stimulus can be a tingling sensation; it need not be an electrical shock. Addictions that have been successfully with aversion-therapy stimuli include cocaine, methamphetamine, marijuana, and nicotine. In these types of aversion therapy using counter conditioning, the aversive stimulus can either be manually triggered by the subject or by an observer.

The same principle can be used to control animal behavior. An example is providing a high-pitched sound aversive to a dog when the dog gets close to a forbidden area In an example in the prior art, a negative stimulus such as an electric shock has been triggered when a subject physically touches an object such as an electrified fence. In an alternative approach, Janning, et al., U.S. Pat. No. 6,166,643, "Method and apparatus for controlling the whereabouts of an animal", teaches how an aversive stimulus is delivered to an animal if a predetermined boundary is encroached under predetermined conditions. Marischen, et al., U.S. Pat. No. 5,351,653, "Animal training method using positive and negative stimuli" provides for a positive or negative sound stimulus triggered manually by an observer where the sound emitter is either at the site of the observer or on a collar worn by the animal. In Custer, U.S. Pat. No. 5,353,744, "Animal control apparatus," a portable receiver and stimulator is attached to an animal that is activated when the animal encroaches on a boundary and a related transmitter. These systems do not employ RFID tags.

Electronic-Impulse Counter-Conditioning (also known as Faradic aversion therapy) has been used in the treatment of alcoholism (Smith, J. W., & Frawley, P. J., "Long-Term Abstinence from Alcohol in Patients Receiving Aversion Therapy as Part of a Multimodal Inpatient Program," *Journal of Substance Abuse Treatment*, 7:77-82, 1990), nicotine (Smith, J. W., "Long-Term Outcome of Clients Treated in a Commercial Stop Smoking Program," *Journal of Substance Abuse Treatment*, 5:33-36, 1988), and methamphetamine and cocaine (Frawley, P. J., & Smith, J. W., "One-Year Follow-Up after Multimodal Inpatient Treatment for Cocaine and Methamphetamine Dependencies," *Journal of Substance Abuse Treatment*, 9:271-286, 1992.).

Previous RFID patents related to RFID systems in medical systems include Yarin et al, U.S. Pat. No. 6,380,858, "Systems and methods for monitoring patient compliance with medications" and Yarin et al., U.S. Pat. No. 6,294,999, "Systems and methods for monitoring compliance with medication regimens" both of which used medication containers with RFID tags and Smart Trays with RFID readers. The Smart Tray (a) provides signals to the patient of when to take medications and how much, (b) monitors when the medication container is removed, and (c) can communicate its report on patient compliance with or more parties such as healthcare provides or pharmacies.

Other medication dispensing inventions are addressed in De La Huerga, U.S. published patent applications 20010028308 and 20030099158, "Interactive medication container" which use the RFID tag as a container ID, alerts the patient to take the medicine, and records the time the container is removed from its place, Rand, U.S. patent application 20020189612, "Medicament dispenser," and Bonney et al., U.S. patent application 20030079744, "Medicament dispenser," from the same firm, that use the RFID tag to determine the identification of a medicament container, and Klein, U.S. published patent application 20020026330, "System and method for patient medication management and compliance using a portable computing device" which uses RFID tags to determine the identification of a medicament container. None of these incorporate stimuli used for behavioral modification.

Other health-related systems are Gutta et al., U.S. patent application 20020169583, "Automatic system for monitoring person requiring care and his/her caretaker" that checks patient status and uses an RFID tag associated with a subject in lieu of a biometric identifier such as a thumb print and Kaylor et al. U.S. patent application 20040078219 "Healthcare networks with biosensors" which uses RFID tags for product identification. Neither of these incorporate stimuli used for behavioral modification. In addition, neither RFID reader nor an RFID tag is ever on the subject.

Previous inventions in aversive therapy include Pope, U.S. Pat. No. 3,963,033, "Electronic smoking inhibiting device" which in response to the opening of a container containing cigarettes delivers an alarm sound after a predetermined delay period followed by a faradic shock. Regal, U.S. Pat. No. 4,163,449, "Enuresis treatment device" employs a urine-detection pad to detect bed wetting which causes the triggering of an aversive alarm. Another invention using aversive stimuli is Nemir, U.S. Pat. No. 4,995,404, "Apparatus for treating bruxism" that delivers an electric shock or an alarm in response to the user's bruxing events. In Israel, et al., U.S. Pat. No. 5,304,211, "Apparatus for administering electrical aversive stimulus and associated method," a therapist using a transmitter remotely triggers an aversive stimulus delivered to a subject via a receiver/stimulator driving an electrode. In Silverman, et al., U.S. Pat. No. 5,243,998, "Automatic operant conditioning system," a biofeedback system is described in which the subject controls a variable such as posture that is measured and then processed by a microcomputer that compares the measurement to criteria and depending on the result a positive or negative stimulus (such as an audio tone) delivered. None of these inventions in the prior art use RFID tags.

In the domain of location of beings, Levine in U.S. Pat. Nos. 6,334,073 and 6,154,676, "Internal monitoring and behavior system" determines whether a subject is inside or outside a defined area, and if the subject is outside that area, an internal system activates a stimulating electrode or chemical micropump to produce an aversive stimulus to the subject. Levine in U.S. Pat. No. 6,034,622, "Location monitoring via implanted radio transmitter" determines whether a subject is outside a given area, but does not provide for an aversive stimulus to be delivered but instead provides the information to a monitoring system. Again these inventions do not involve the use of RFID.

BACKGROUND OF THE INVENTION—OBJECTS AND ADVANTAGES

Several objects and advantages of the present invention are:

(a) one or many entities can be easily and inexpensively tagged, (b) numerous form factors are available at increasingly lower cost because RFID tags are being used in logistic and other applications, (c) provides flexibility since objects can be identified without necessarily being touched, (d) provides variation in response to the object depending on which person or animal gets in proximity to the tag, (e) supports aversive stimuli, appetitive stimuli, and event recording, (f) provides automatically rather than manually generated stimuli, (g) provides wireless or wired connections, (h) supports either immediate or delayed stimuli, (i) provides for variation of stimulus level, type, timing, and pattern, (j) supports variation of level of stimulus by the subject, (k) supports single, multiple simultaneous and multiple serial stimulations, (l) provides for criteria to be applied to short-term, real-time patterns or pattern analysis of Logged events, (m) allows data to be recorded in a writable tag for later analysis or interrogation, (n) supports both short and long-distance configurations, and (o) provides a common mechanism for determining whether a stimulus should be triggered, but what that stimulus is (e.g., an electric tingling sensation in Electronic-Impulse Counter-Conditioning vs. release of a noxious odor) can be determined separately.

SUMMARY

The present invention uses RFID tags attached to subjects or objects, RFID readers attached to subjects or kiosks, and stimulus generators and output devices on subjects or kiosks. Here the term kiosk can refer to an actual kiosk or another suitable enclosure. An example is a configuration in which an RFID tag is attached to an object to be avoided or be sought and a portable RFID reader, host computer, stimulus generator, and output device worn by the subject. When the subject comes within range (or even touches the tag), an event is recorded in the host computer associated with the RFID reader and/or an action such as providing a positive or negative stimulus to the subject occurs. Either passive or active RFID tags can be used. Passive RFID tags obtain their power wirelessly from the RFID reader. Active RFID tags obtain their power from a local power source such as a battery. Tags that are read-only simply provide information back to the reader as to what object the reader is near. Those tags that are read/write can also store some information within the tag itself (such as the number of times a reader was near).

Electronic-Impulse Counter-Conditioning can be applied if a subject person wishes to stop smoking. Smoking is an addiction which in broad terms can be viewed as having both nicotine dependence and non-nicotine-related behaviors. The latter include pleasurable experiences in anticipation of smoking, such as crinkling the cellophane taken from the cigarette package. If the RFID-mediated negative stimulus is triggered by the person touching a cigarette package, the pairing of that stimulus and that act can lead to the extinguishment of that non-nicotine-dependence-related behavior. This process can be used in conjunction with nicotine-replacement products such as the nicotine patch for the nicotine-withdrawal component of the smoking addiction as well as web-medicated, telephone, or in-person support programs. The significance of smoking in terms of health and economic impact is significant. Potential application of my RFID system for automatically triggering and delivering stimuli is huge in that there are some 50 million smokers in the U.S. alone, approximately 80% wish to quit, and 69% intend to try and stop smoking within the next year.

My RFID system for automatically triggering and delivering stimuli can be used in the administration of medicaments if an appetitive or aversive stimulus were given to the subject when that subject is a patient near a medication container to remind or condition the patient to take his or her medication or not to take an inappropriate drug. Variation in the stimulation could indicate which medicament and how much. Alternatively when the patient is at a predetermined location or one of predetermined locations (perhaps at a certain time) a stimulus can be used to condition or remind.

My RFID system for automatically triggering and delivering stimuli can be used in weight control, although to this point use of behavioral modification in dieting has not been considered successful. An example of an application in weight control is the subject getting into the close proximity of or touching of the handle of a refrigerator or a container of food triggering a negative response and/or recording the event for later feedback either via a stimulus or a report.

My RFID system for automatically triggering and delivering stimuli does not cover tracking in the form of tracking buying behaviors that is well covered in the prior art. It does, however, cover situations where events are logged so, based on patterns of those events, feedback can be given to the subject at a later time.

My RFID system for automatically triggering and delivering stimuli is not limited to type of aversive or appetitive stimulus, nor the scheduling of that stimulus, nor the condition for which the aversive or appetitive stimulus is being applied.

DRAWINGS—FIGURES

Figure 1A:
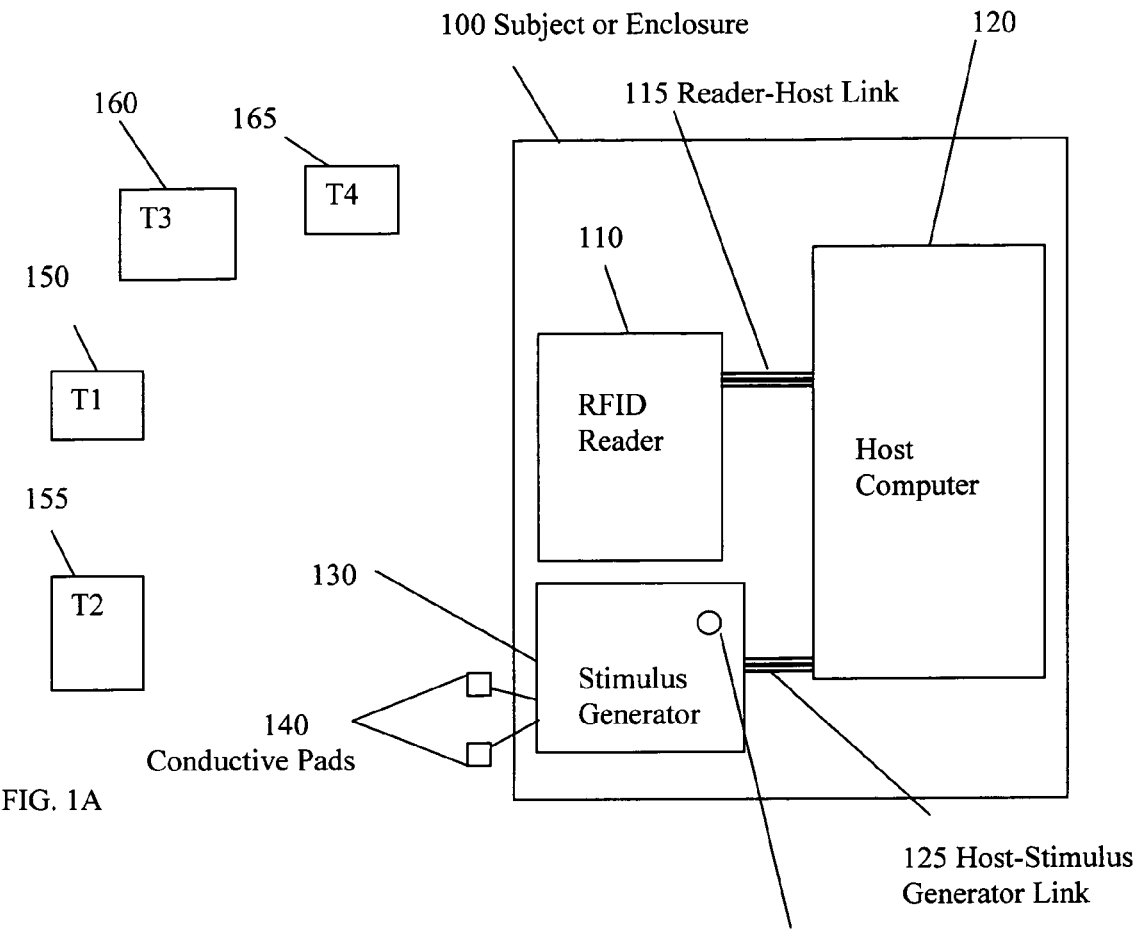
FIG. 1A shows a system with RFID tags on objects and the active components of the system such as the RIFD reader, host computer, stimulus stimulator, and conductive pads on a subject.

DRAWINGS—REFERENCE NUMERALS 100 subject or kiosk or other suitable enclosure
110 RFID reader
115 link between RFID reader and host computer
120 host computer
125 link between host computer and stimulus generator
130 stimulus generator
135 potentiometer to vary stimulus intensity
140 conductive pads
150, 155, 160, 165, 175, 180, 185, 190 RFID tags
225 scent-generating device
265 light-generating device
295 sound-generating device
300 kiosk or equivalent
310 RFID reader
315 link between RFID reader and host computer
320 host computer
325 link between host computer and stimulus generator
330 stimulus generator
335 stimulus-delivery device
350 subject
355 RFID tag
425 link between host computer and RF transmitter
430 RF transmitter
435 transmission antenna
440 reception antenna
443 RF receiver
445 stimulus generator
447 potentiometer to vary stimulus intensity
449 conductive pads

DETAILED DESCRIPTION

FIGS. 1A, 1B, 2A-2D—Preferred Embodiments

The primary preferred embodiment is shown in FIG. 1A. The subject 100 wears the components contained within the box. An RFID reader 110 (e.g., Model S2000 Micro Reader from Texas Instruments) outputs RF which energizes passive RFID tags, 150, 155, 160, and 165 which in turn causes those tags emit their IDs. Each ID is unique and is directly mapped to the object to which the given tag is attached (e.g., a package of cigarettes). Those IDs are read by RFID reader 110 which is interfaced to and controlled by host computer 120 via link 115 that causes the RFID reader 110 to interrogate the RFID tags and subsequently both records the events and through link 125 turns on a stimulus generator (e.g., Omron Sport Massager, Model HV-F002A, Omron Healthcare, Inc., Vernon Hills, Ill.) 130. The contacts of its on-off switch are connected in parallel by closing the circuit with the stimulus generator. This Transcutaneous Nerve Stimulation (TENS) apparatus is authorized for over-the-counter (OTC) use and does not require a prescription. Thus it could easily be employed in consumer versions of the present invention. It is understood that the host computer can be any suitable device such as a microcontroller. Criteria are evaluated within the host computer to determine whether a stimulus should be generated, and if so, of what type. These criteria deal with such factors as timing of one event to another and can include time of day. In this embodiment, stimulus generator 130 outputs electrical impulses that are transmitted through conductive pads 140 attached, for example, to the forearm of the subject. The level of the electrical stimulus (usually a tingling sensation, rather than a shock) fed back can be set by the subject, either by a potentiometer 135 on the stimulus generator or in another embodiment by control from the host computer. The RFID tags themselves (whether passive or active) can also be disabled by permanently "killing" or removing them after their use is not needed or alternatively turning their use on and off by including their IDs or not including their IDs in the list for recognition in the host computer 120 or in the RFID reader 110. In any of the embodiments discussed, a combination of events as evaluated in the host computer may elicit the type of stimulus. For example, detection of event A (say the touching of a container of alcohol) may not trigger a stimulus, but the detection of event A followed by event B (the opening of the container say detected by a RFID tag on the opening of the container being no longer detected because it has been removed) would trigger a stimulus. Time of day may be a factor. An example is a patient getting close to a given location at a time of day at which they need to take their medication being given an appetitive stimulus as a reminder. This pattern analysis occurs in real-time based on events occurring (but not limited to being) over a short period of time as opposed to pattern detection based on logged events described below in another embodiment. The timing and type of stimulus are determined in the host computer. The described systems can be used in a medical context using patients or a more general context using subjects. In another embodiment, the host computer can be attached to a more powerful computer (not shown) or one with access to more information (not shown) that works in concert with the host computer or controls the host computer.

Figure 1B:
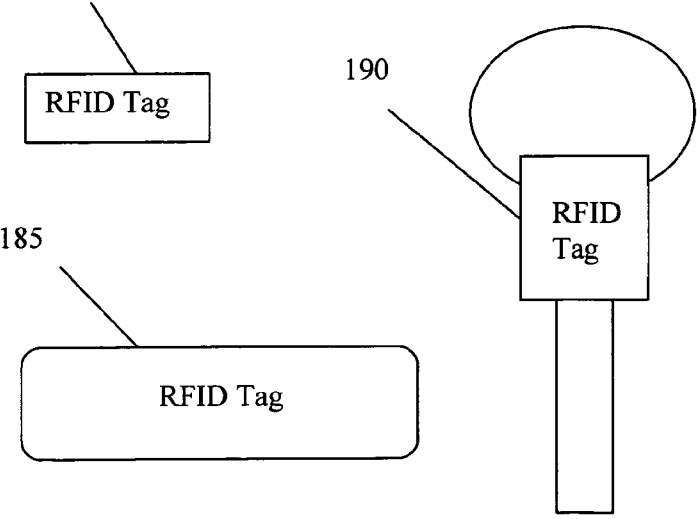
FIG. 1B shows RFID tags of various physical formats.

It is practical to implement RFID tags into a wide range of sizes and shapes. FIG. 1B shows some various physical formats of RFID tags of the type by Texas Instruments (TI). For example, 175 shows a disk transponder (TI model RI-TRP-R9QL), 180 shows a wedge transponder (TI model RI-TRP-R9WK), 185 shows a glass transponder (TI model RI-TRP-IR2B), and 190 shows a key-fob transponder (TI model RI-TRP-RFOB). The preceding tags operate at 134 kHz; other frequency bands can be used for RFID systems (e.g., 13.56 MHz, 860 to 930 MHz and 2.45 GHz). Function may follow form. For example, if a negative stimulus is to be fed back to someone who should not be driving, then having an RFID tag built into a key fob is an effective design. Tags come in different form-factor shapes that can facilitate their placement and thus overall utility. In addition, an increasing number of products will come with at least packages that have RFID tags already attached for tracking purposes and can be used in my RFID system for automatically triggering and delivering stimuli without placing them as a separate step with additional cost.

Related RFID tags might be placed, such as one RFID tag on the mouth of a container of alcohol and another attached on a piece of clothing a subject is wearing located near the subject's mouth, or alternatively attached to the subjects skin near the mouth. Another embodiment has placement of RFID tags on both the object and the subject. An alternative embodiment includes a plurality of RFID tags placed on different objects, say multiple containers of liquor in the case of someone trying to stop drinking, each of which can be detected and that detection processed with a resultant stimulus.

While active RFID tags can be used in the stimulus systems covered in this invention, passive tags are less expensive and will meet many of the needs of such systems. When active tags are utilized, say for longer ranges, the diagram shown in FIG. 1A applies except that the tags 150, 155, 160, and 165 have their own power supplies (e.g., batteries) rather than being energized by RF supplied by the RFID reader 110.

In an alternative embodiment, RF Communication is used for recording events on another system instead of the "portable" host.

Figure 2A:
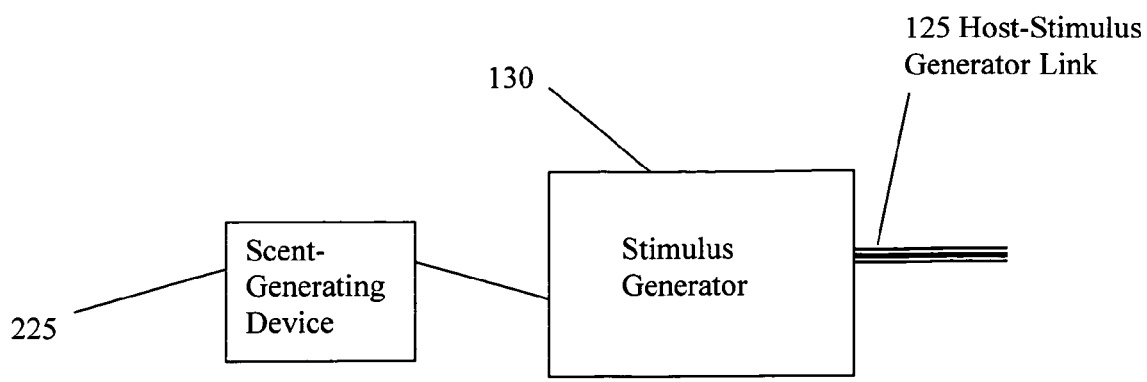
FIGS. 2A to 2C shows alternative output modes, scent, light, and sound.
Figure 2B:
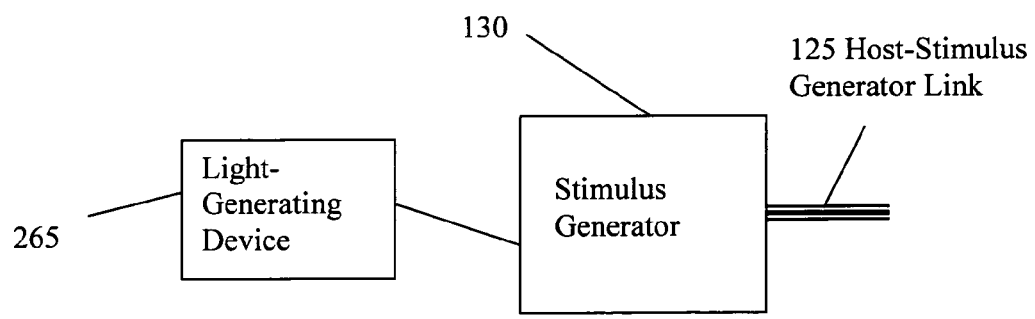
Figure 2C:
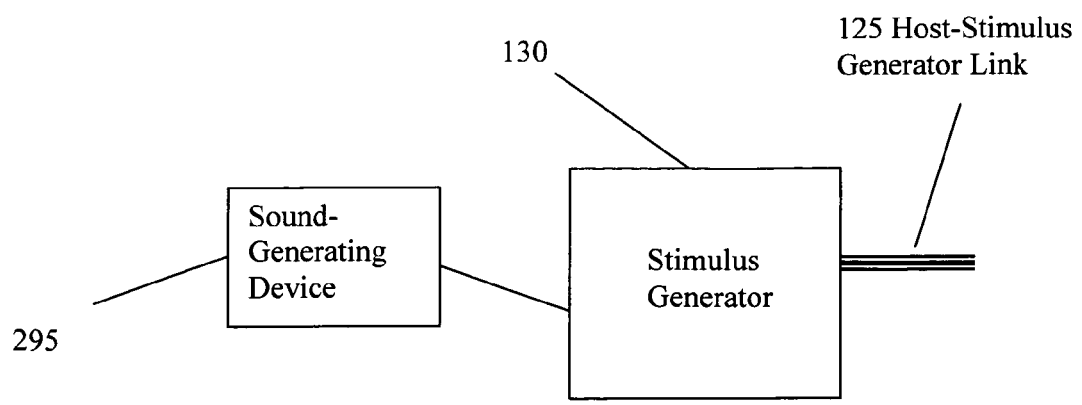

An alternative embodiment of the output of stimulus, one involving the output of an odor, is shown in FIG. 2A. This shows the conductive pads 140 in FIG. 1A replaced by a scent-generating device 225 (The Scent Dome, Trisenx Holdings, Inc., Savannah, Ga.). Again, the stimulus generator 130 is connected to the host computer by link 125. Another embodiment of the output stimulus, one involving output of light, is shown in FIG. 2B. Again, the stimulus generator 130 in FIG. 1A is connected to the host computer through link 125. In this case, a light-generating device 265 replaces the conductive pads 140 in FIG. 1A. An alternative embodiment of the output stimulus, one involving output of sound, is shown in FIG. 2C. Again, the stimulus generator 130 in FIG. 1A is connected to the host computer via link 125. In this case, a sound-generating device 295 replaces the conductive pads 140 in FIG. 1A. Other output modalities such as touch, hitting, or a pinch are alternative embodiments or the delivery of an object such as a piece of candy. In the latter case, the stimulus generator 295 in FIG. 2C causes a little door to open or a chute to discharge the given object.

Figure 2D:
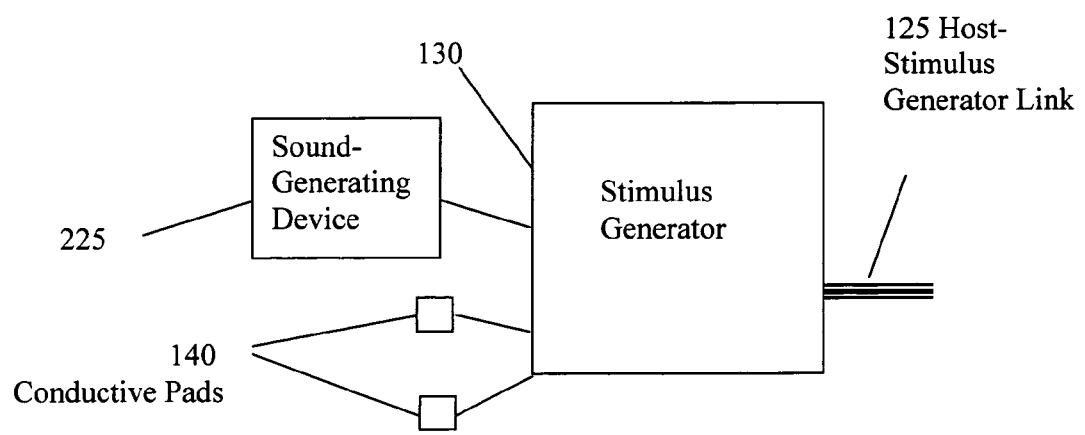
FIG. 2D shows version with two modes of output.

In another embodiment, multiple stimuli can result from the action of a patient. For example, both an electrical stimulus and an odor can be delivered as shown in FIG. 2D in which the stimulus generator 130 is interfaced to the host computer by link 125 and has two output modes, one the conductive pads 140 and the other a scent-generating device 295. Examples of negative stimuli are electric shock, tingling sensation, loud noise, or a noxious odor. Examples of positive stimuli are a reward such as a piece of candy, a pleasant sound, or a pleasant odor. In addition to the type of stimulation, including multiple types delivered simultaneously, the pattern of stimulation of stimulation can be varied as well.

In the drawings, the stimulus generator and output device are shown separately for completeness. Alternatively, embodiments can combine them. An example is having the host computer connected to an odor generating device that is both the stimulus generator and the output device. In the case of electrical stimulation, the stimulus generator 130 in FIG. 1A generates the electrical stimulus, but that stimulus can be viewed as being delivered by conductive pads 140.

An alternative embodiment of the invention is also represented by FIGS. 1A, 2A-2D. In this case 100 represents a kiosk or other suitable enclosure and the subject is separated from the apparatus except that if an electric stimulus is to be delivered, the conductive pads 140 attached to the subject are connected to the stimulus generator by an electrical cable or there is a wired or wireless link (RF, infrared, or other) between an output device or a stimulus generator plus output device on the subject and the stimulus generator or host computer in the kiosk or other suitable enclosure respectively.

Figure 3:
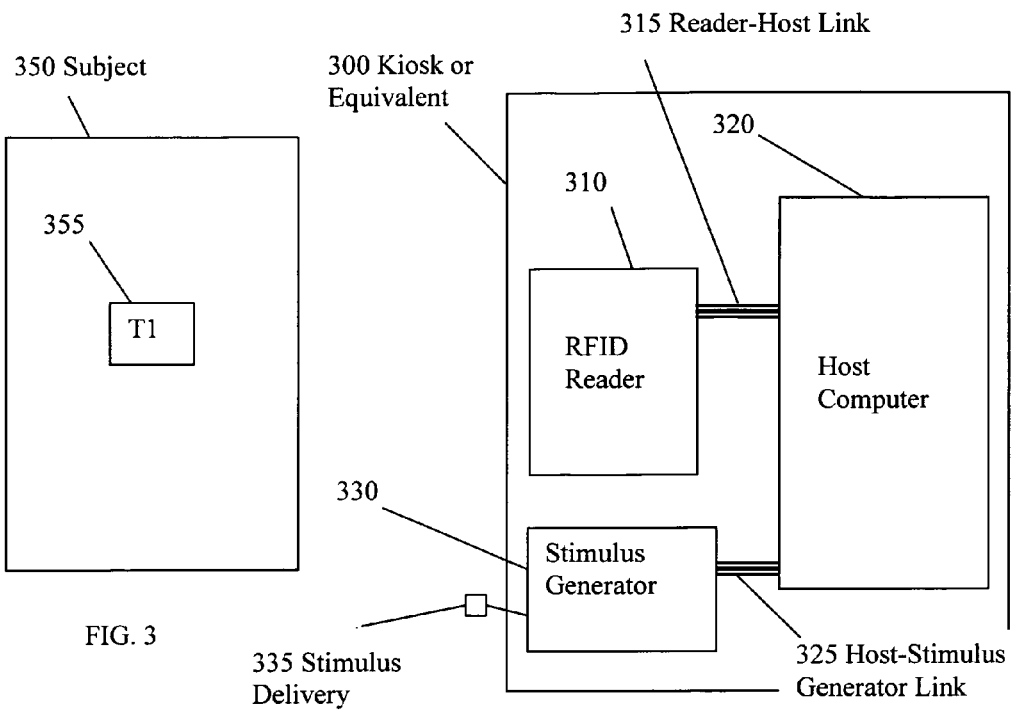
FIG. 3 shows a system with the RFID tag on the subject and the active components of the system such as the RIFD reader, host computer, stimulus stimulator, and output device in a kiosk or similar enclosure.
Figure 4:
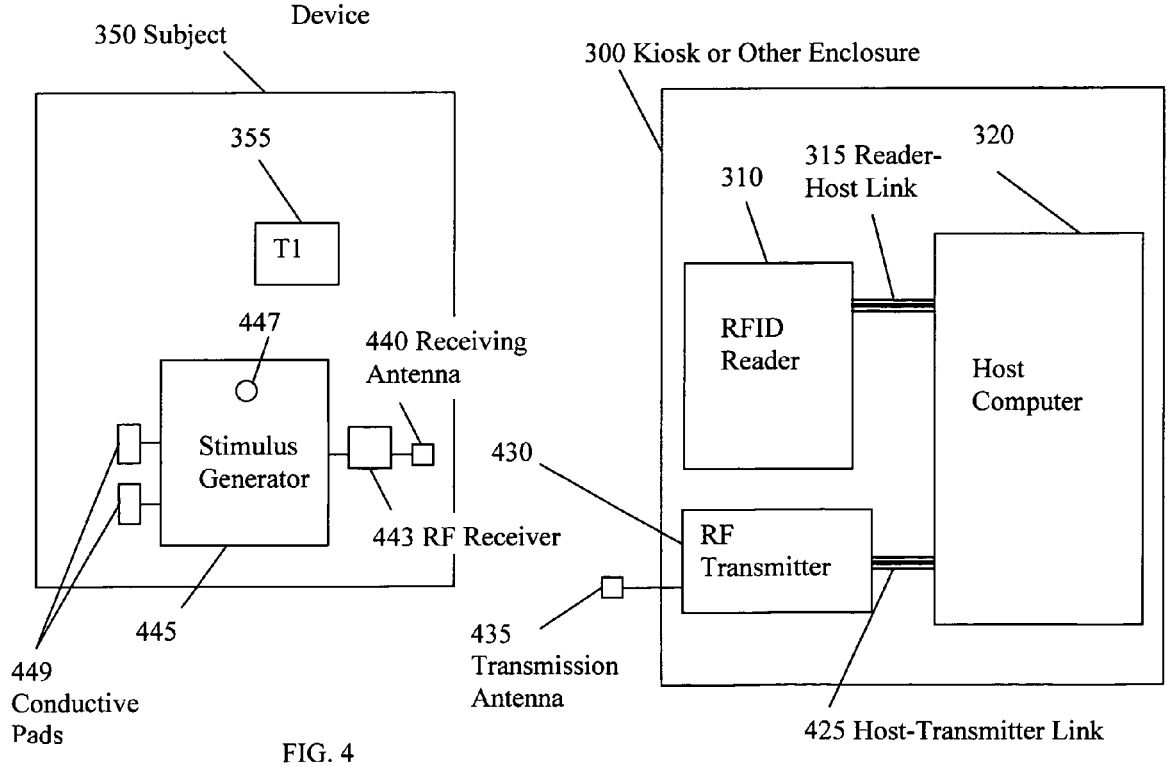
FIG. 4 shows a variation the system shown in FIG. 3 in which the stimulus generator and output device are on the subject and the connection between the subject and the kiosk or other enclosure use RF communications.

FIGS. 3-4 Additional Embodiments

An alternative embodiment is shown in FIG. 3. RFID tag 355 in this embodiment is worn by the subject (person, animal, robot, or autonomous agent) 350. This configuration detects when the subject close enough to the RFID reader so that the RFID tag is detected and, if appropriate, a stimulus triggered. The RFID reader and associated components are housed in a kiosk (or other suitable enclosure) 300. An example of this configuration is where the enclosure is attached to a beverage refrigerator containing beer in the situation where the subject is an alcoholic who is attempting to quit using alcohol. The IDs of tags coming in range are recorded by RFID reader 310 which is interfaced to and controlled by host computer 320 via link 315 that causes the RFID reader 310 to interrogate the RFID tags and subsequently both records the events and through link 325 turns on the stimulus generator 330 which is connected to output device 335. In this embodiment, stimulus generator 330 outputs a stimulus remotely deliverable via output device 335 to the subject such as, but not limited to, scent, light, sound, including speech, heat, cold, mechanical including pinching, injection of a medicament, injection into the mouth of a substance causing taste, or delivery. Alternatively, an electrical cable can deliver a stimulus to conductive pads on the subject.

Yet another alternative embodiment of the invention is shown in FIG. 4. The configuration and its application are the same as in FIG. 3 except for the handling of the stimulus generation and delivery. In this hybrid approach to the embodiment of FIG. 3, the subject (person, animal, robot, or autonomous agent) 350 wears RFID tag 455 and the RFID reader and associated components are housed in a kiosk (or other suitable enclosure) 300. The IDs of tags coming in range are recorded by RFID reader 310 which is interfaced to and controlled by host computer 320 via link 315 that causes the RFID reader 310 to interrogate the RFID tags and subsequently both records the events and through link 425 controls the RF transmitter 430 and its antenna 435. RF output from transmitting antenna 435 is received by antenna 440 that is connected to receiver 443 and the triggering signal then sent to stimulus generator 445 that delivers a stimulus such as an electric tingling sensation via conductive pads 449 or one or more of the alternative stimuli such as scent, light, or sound discussed in connection with FIGS. 2A-2D. If the level of stimulus is to be set by the subject, this can be accomplished through potentiometer 447. In alternative embodiments, the wireless connection between the apparatus in the enclosure and the feedback apparatus on the subject is by infrared, other optical or audio mechanism instead of a radio-frequency mechanism. In an alternative embodiment, the connection between the apparatus in the enclosure and the feedback apparatus on the subject is via a wired rather than a wireless connection. In alternative embodiments, both the stimulus generator and the output device are located on the subject rather than in the separate enclosure and the connection between the host computer in the enclosure and the stimulus generator on the subject is connected using either a wireless or wired mechanism.

Additional embodiments are those in which the output device connected to the stimulus generator results in the injection of a drug, human speech say by use of a text-to-speech module, or the injection of a substance into the mouth causing a positive or negative taste.

In another embodiment, the events may be logged, and depending on the pattern (perhaps including trend), information fed back to the subject by a mechanism such as, but not limited to, a computer display, hardcopy, light display, odor generation, mechanical pressure, or sound pattern, or speech at a later point in time. Such analysis may include the detection of complex patterns from which complex inferences are drawn. For example event A followed by event B may cause one stimulus or lack of stimulus to be generated, while one or more of events A alone may not. Say in the case of an individual wishing to quit smoking, crinkling of the cellophane wrapper from a cigarette package (event A) may or may not be followed by taking out and touching a cigarette (event B). Event B in conjunction with event A would generate one type of negative stimulus while event or events A alone would generate a different type of negative stimulus or none at all.

Another embodiment involves GPS used to determine a motor-vehicle location and detect inappropriate behavior such as speeding. In this embodiment, the GPS substitutes for RFID tag and reader and there is a wireless connection between a computer associated with the GPS and the host computer of previous embodiments. The host computer, stimulus generator, output device, and associated components are as described in previous embodiments. The output device delivers aversive feedback, say a light or mild tingling sensation, to associate the negative stimulus with the undesired act.

Within the relatively short range of the passive tag, adjustments can be made to make the effective range even shorter if that would improve the situation. This can be done by applying RF shielding to the tag or to the transmitted output of the reader.

In one embodiment, the action is recorded in the read-write tag. In another embodiment, the action is recorded on the host computer for the RFID reader. In a third, the action is recorded at both locations. One reason for in-tag event recording is that multiple RFID reader sources can be recorded. An example of such use is the recording within the read-write tag of the total number of accesses to a refrigerator by a family. Each family member is associated with his or her own RFID reader. Another embodiment uses read-write RFID tags that have individual counters record events for each subject. This is a process of "instrumenting" objects that are important in selected behaviors. Tags can be attached to various objects and the presence of each object will be appropriately recorded. The detection of the presence of an RFID tag may just be recorded in addition to, or instead of, providing an immediate feedback stimulus.

The reader can see my RFID system for automatically triggering and delivering stimuli provides that one or many entities can be easily and inexpensively tagged where RFID tags are available in numerous form factors at increasingly lower cost because RFID tags are being used in logistic and other applications. The invention provides flexibility since objects can be identified without necessarily being touched and supports variation in response to the object depending on which person or animal gets in proximity to the RFID tag. Aversive stimuli, appetitive stimuli, and event recording are automatically rather than manually generated where stimuli can be delivered immediately or after a delay. Data can be recorded in a writable RFID tag for later analysis or interrogation. Both wireless and wired connections are supported. Criteria can be applied to short-term patterns. Time of day can be considered. Pattern analysis of logged events is supported. Either short or longdistance configurations can be utilized. The invention has the additional advantages gained by flexibility in the way stimuli are delivered as evidenced by the ability to support
  variation of stimulus level, type, timing, and pattern,
  variation of level of stimulus by the subject, and
  single, multiple simultaneous, and multiple serial stimulations.

My RFID system for automatically triggering and delivering stimuli provides a common mechanism for determining whether a stimulus should be triggered, but what that stimulus is (e.g., an electric tingling sensation in Electronic-Impulse Counter—Conditioning vs. release of a noxious odor) can be determined separately.

Although the description above contains many specificities, these should not be construed as limiting the scope of the invention but as merely providing illustrations of some of the presently preferred embodiments of this invention. For example, the RFID reader and the host computer can be combined into a single unit or the enclosure for the apparatus can be a container built into the side of a building.

Thus the scope of the invention should be determined by the appended claims along with their full scope of legal equivalents, rather than the examples given.

What is claimed is:

1. A method for providing behavioral feedback to a subject comprising:
  (a) detecting the presence of a Radio-Frequency ID (RFID) tag located on an entity that is to be avoided or sought by said subject using an RFID reader interfaced to a host computer, (b) sending a control signal to a stimulus generator by and at a time and type determined by said host computer when the criteria for applying negative/aversive or positive/appetitive feedback to said subject incorporated in said host computer are met, and (c) delivering a generated stimulus thus providing negative or positive feedback to said subject via an output device driven by said stimulus generator.

2. The method for behavioral feedback conditioning in claim 1 comprising:

(a) detecting the presence of the Radio-Frequency ID (RFID) tag located on an object using the RFID reader located on the subject interfaced to the host computer located on said subject, (b) sending the control signal to the stimulus generator located on said subject by and at a time and type determined by said host computer when the criteria incorporated in said host computer are met, and (c) delivering a generated stimulus output to said subject via the output device located on said subject where said generated stimulus output selected from the group consisting of electrical, audio including speech, odor, light, heat, cold, mechanical, injection of a medicament, injection into the mouth of a substance causing taste, and delivery of the object.

3. The method for behavioral feedback conditioning in claim 1 comprising:

(a) detecting the presence of the Radio-Frequency ID (RFID) tag located on an object using the RFID reader located in an enclosure separate from the subject interfaced to the host computer located in said enclosure, (b) sending the control signal to the stimulus generator located in said enclosure by and at a time and type determined by the host computer when the criteria incorporated in said host computer are met, and (c) delivering a generated stimulus output to the subject via the output device located on said subject and interfaced to said stimulus generator using a communications means where said generated stimulus output selected from the group consisting of electrical, audio including speech, odor, light, heat, cold, mechanical, injection of a medicament, injection into the mouth of a substance causing taste, and delivery of an object, and said communications means selected from the group consisting of wired and wireless.

4. The method for behavioral feedback conditioning in claim 1 comprising:

(a) detecting the presence of the Radio-Frequency ID (RFID) tag located on an object using the RFID reader located in an enclosure separate from the subject interfaced to the host computer located in said enclosure, (b) sending the control signal to the stimulus generator located on said subject by and at a time and type determined by said host computer interfaced to said stimulus generator using a communications means when the criteria incorporated in said host computer are met and where said communications means selected from the group consisting of wired and wireless, and (c) delivering a generated stimulus output to said subject via the output device located on said subject where said generated stimulus output selected from the group consisting of electrical, audio including speech, odor, light, heat, cold, mechanical, injection of a medicament, injection into the mouth of a substance causing taste, and delivery of the object.

5. The method for behavioral feedback conditioning in claim 1 comprising:

(a) detecting the presence of the Radio-Frequency ID (RFID) tag located on the subject using the RFID reader located in an enclosure separate from said subject interfaced to the host computer located in said enclosure, (b) sending the control signal to the stimulus generator located in said enclosure by and at a time and type determined by said host computer interfaced to said stimulus generator using a communications means when the criteria incorporated in said host computer are met and where said communications means selected from the group consisting of wired and wireless, and (c) delivering a generated stimulus output to the subject via the output device located in said enclosure separate from said subject where said generated stimulus output selected from the group consisting of electrical, audio including speech, odor, light, heat, cold, mechanical, injection of a medicament, injection into the mouth of a substance causing taste, and delivery of an object.

6. The method for behavioral feedback conditioning in claim 1 comprising:

(a) detecting the presence of the Radio-Frequency ID (RFID) tag located on the subject using the RFID reader located in an enclosure separate from said subject interfaced to the host computer located in said enclosure, (b) sending the control signal to the stimulus generator located in said enclosure by and at a time and type determined by said host computer when the criteria incorporated in said host computer are met, and (c) delivering a generated stimulus output to said subject via the output device located on said subject interfaced to said stimulus generator using a communications means and where said communications means selected from the group consisting of wired and wireless where said generated stimulus output selected from the group consisting of electrical, audio including speech, odor, light, heat, cold, mechanical, injection of a medicament, injection into the mouth of a substance causing taste, and delivery of an object.

7. The method for behavioral feedback conditioning in claim 1 comprising:

(a) detecting the presence of the Radio-Frequency ID (RFID) tag located on the subject using the RFID reader located in an enclosure separate from said subject interfaced to the host computer located in said enclosure, (b) sending the control signal to the stimulus generator located on said subject by and at a time and type determined by said host computer when the criteria incorporated in said host computer are met using a communications means between said host computer and said stimulus generator and where said communications means selected from the group consisting of wired and wireless, and (c) delivering a generated stimulus output to said subject via the output device located on said subject where said generated stimulus output selected from the group consisting of electrical, audio including speech, odor, light, heat, cold, mechanical, injection of a medicament, injection into the mouth of a substance causing taste, and delivery of an object.

8. The method for behavioral feedback conditioning in claim 1 wherein stimulus generator and output device are combined.

9. The method for behavioral feedback conditioning in claim 1 wherein RFID identification means are placed on one or a plurality of subjects and one or more or a plurality of objects.

10. The method for behavioral feedback conditioning in claim 1 wherein means of type of stimulus selected from the group consisting of aversive and appetitive.

11. The method for behavioral feedback conditioning in claim 1 wherein subject selected from the group consisting of human, animal, robot, and autonomous agent.

12. The method for behavioral feedback conditioning in claim 1 wherein means of variation of stimulus selected from the group consisting of level, timing and pattern.

13. The method for behavioral feedback conditioning in claim 1 wherein means provides for multiple simultaneous stimuli where said multiple simultaneous stimuli selected from the group consisting of varying level, varying type, varying timing, and varying pattern.

14. The method for behavioral feedback conditioning in claim 1 wherein means provides for multiple serial stimulations where said multiple serial stimulations selected from the group consisting of varying level, varying type, varying timing, and varying pattern.

15. The method for behavioral feedback conditioning in claim 1 wherein means of stimulus delivers the stimulus with timing selected from the group consisting of immediate and after a delay.

16. The method for behavioral feedback conditioning in claim 1 wherein host computer means also records the events.

17. The method for behavioral feedback conditioning in claim 1 wherein there is a means for the subject to adjust the level of the stimulus.

18. The method for behavioral feedback conditioning in claim 1 wherein feedback means is selective as to which subject gets or which subjects get feedback.

19. The method for behavioral feedback conditioning in claim 1 wherein recording means is selective as to which subject's events recorded.

20. The method for behavioral feedback conditioning in claim 1 wherein triggering means is selective as to an object.

21. The method for behavioral feedback conditioning in claim 1 wherein enabling means is selective as to when the system is enabled versus disabled.

22. The method for behavioral feedback conditioning in claim 1 wherein means causes stimulation to occur immediately based on the analysis of short-term patterns.

23. The method for behavioral feedback conditioning in claim 1 wherein means of stimulation occurs at a later point in time after detection of RFID-tagged events based on pattern analysis of logged events.

24. The method for behavioral feedback conditioning in claim 1 wherein means of delivered feedback selected from the group consisting of computer display, hardcopy, light display, odor generation, mechanical pressure, sound pattern, and speech.

25. The method for behavioral feedback conditioning in claim 1 wherein the RFID tag has write capability and data are recorded for later analysis.

26. The method for behavioral feedback conditioning in claim 1 wherein host-computer means is interfaced to another computer with which said host computer works in concert.

27. The method for behavioral feedback conditioning in claim 1 wherein means of long-distance identification is used via GPS or other remote means.

* * * * *